(12) United States Patent
Hartlove (10) Patent No.: US 7,787,663 B2
(45) Date of Patent: *Aug. 31, 2010

(54) SYSTEM AND METHOD FOR DETECTING THERMAL ANOMALIES

(75) Inventor: Jason Hartlove, Los Altos, CA (US)

(73) Assignee: Aptina Imaging Corporation, Inc., Grand Cayman (KY)

(*) Notice: Subject to any disclaimer, the term of this patent is extended or adjusted under 35 U.S.C. 154(b) by 0 days.

This patent is subject to a terminal disclaimer.

(21) Appl. No.: 12/267,981

(22) Filed: Nov. 10, 2008

(65) Prior Publication Data

US 2009/0136093 A1 May 28, 2009

Related U.S. Application Data

(63) Continuation of application No. 11/067,451, filed on Feb. 25, 2005, now Pat. No. 7,457,441.

(51) Int. Cl.
G06K 9/00 (2006.01)

(52) U.S. Cl. .............. 382/115; 382/117; 382/118; 374/121

(58) Field of Classification Search ............... 382/115, 382/117, 118; 374/121
See application file for complete search history.

(56) References Cited

U.S. PATENT DOCUMENTS

| 5,133,605 | A | 7/1992 | Nakamura | |
|---|---|---|---|---|
| 5,603,328 | A | 2/1997 | Zucker et al. | 128/664 |
| 5,963,148 | A | 10/1999 | Sekine et al. | 340/905 |
| 2001/0046316 | A1 | 11/2001 | Miyano et al. | 382/154 |
| 2003/0053664 | A1 | 3/2003 | Pavlidis et al. | |
| 2004/0208230 | A1 | 10/2004 | Lee et al. | 374/208 |

FOREIGN PATENT DOCUMENTS

| EP | 90123677.8 | 12/1990 |
|---|---|---|
| JP | 2002132341 | 5/2002 |
| WO | WO 2005/012860 A1 | 2/2005 |

OTHER PUBLICATIONS

PCT/ EP/2004/051298, International Search Report.
EP 90 12 3677, European Search Report.
Zhang, Yan, China State Intellectual Property Office (SIPO) Examiner, Office Action for CN 200510132366.5, English translation included, Issued Jan. 22, 2010.
Proctor, Stephen, Great Britain Examiner, Examination Report under Section 18(3) for GB0603686.7, Issued Feb. 1, 2010.

*Primary Examiner*—John B Strege
(74) *Attorney, Agent, or Firm*—RatnerPrestia (57) ABSTRACT

A system and method for detecting a thermal anomaly in humans and/or livestock. In one embodiment, the system includes an image capturing component that captures a visual image of incident light in a screening area, the image capturing component further operable to determine a first coordinate in the captured image, such as the location of a person's eyes. The system further includes a radiation capturing component operable to capture a thermal image of incident radiation in the screening area, the radiation capturing component further operable to determine an analysis area in the captured thermal image based upon the first coordinate in the captured light image. Finally, the system includes a processing component for determining thermal characteristics about the analysis area. As a result, if the thermal characteristics correspond to an alarm event, then an alarm may be triggered and the person or animal may be isolated for further health screening.

19 Claims, 5 Drawing Sheets

SYSTEM AND METHOD FOR DETECTING THERMAL ANOMALIES

CROSS REFERENCE TO RELATED APPLICATIONS

This application is a Continuation of U.S. application Ser. No. 11/067,451, filed Feb. 25, 2005, the contents of which are incorporated herein by reference.

BACKGROUND OF THE INVENTION

Detecting infectious diseases in people, such as Severe Acute Respiratory Syndrome (SARS), is an invaluable first step toward preventing the spread of such diseases. Infectious diseases may be easily spread in high traffic areas such as airports and workplaces and are difficult to detect given the busy activity and divergent travel paths or people is such places. Recent efforts to control the spread of SARS, as well as other infectious diseases, have prompted public health officials to develop a rapid screening process to detect individuals who are experiencing the specific symptom of an elevated body temperature that is common to several infectious diseases. If individuals who exhibit an elevated body temperature, i.e., a fever, may be identified prior to boarding an airplane or entering a factory floor, further health screening can be conducted on only the identified individuals thereby saving both time and effort otherwise wasted by further health screening of healthy individuals.

Because high fever is a symptom of SARS and other infectious diseases, health screening systems of the past have used thermal imaging cameras as a means to rapidly identify potential individuals exhibiting an elevated temperature as the individual passes through a checkpoint. In an effort to identify persons potentially carrying an infectious disease, health care officials in several locations worldwide have employed thermal imaging cameras to attempt to measure and analyze the skin temperature of individuals passing through high-risk regions. Individuals exhibiting elevated skin temperatures are then isolated for further evaluation to determine the cause.

Figure 1:
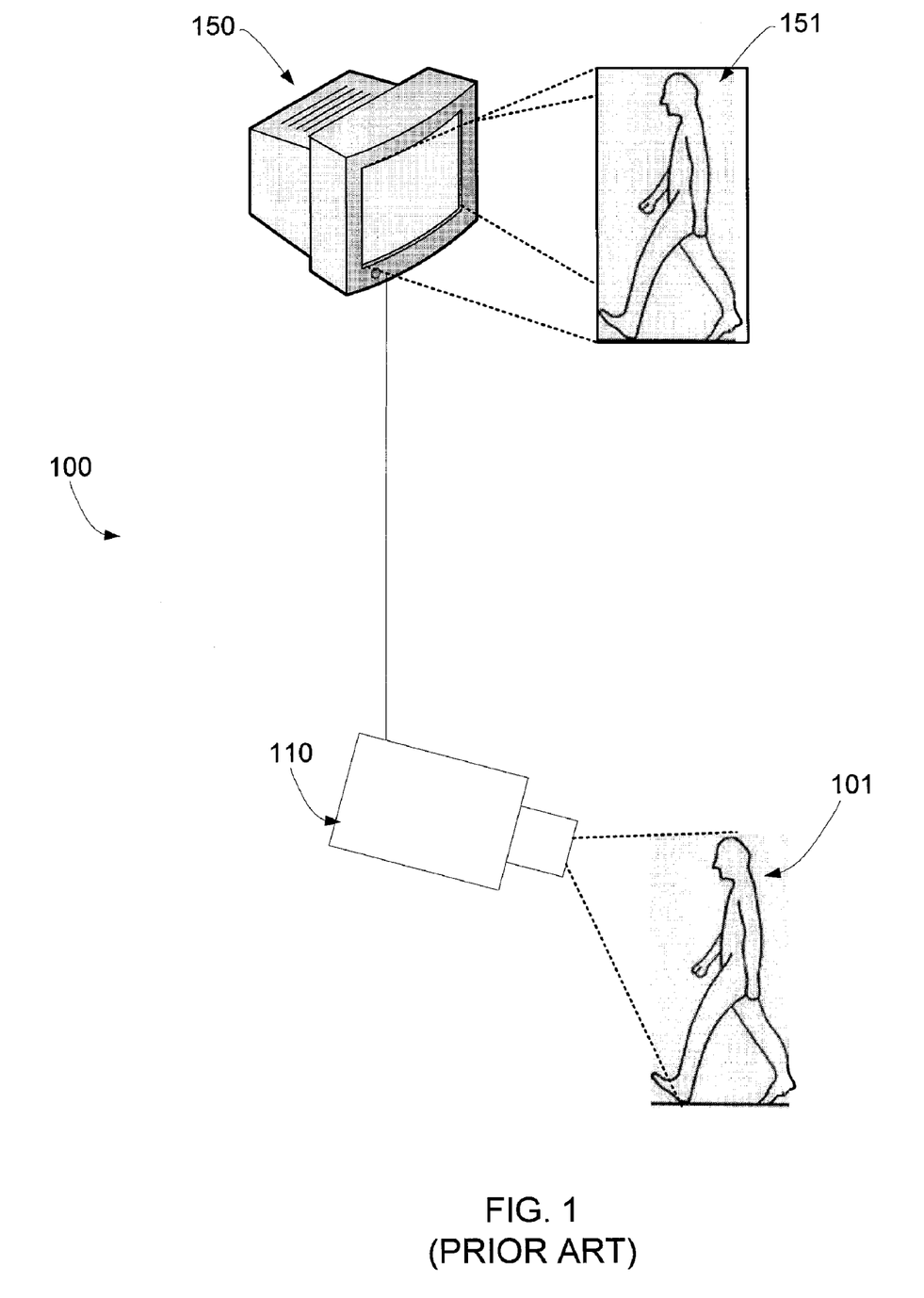
FIG. 1 is a block diagram of a conventional thermal detection system that may be used for detecting elevated skin temperatures, or other thermal anomalies, that may be present within person passing through a screening area.

FIG. 1 is a block diagram of a conventional thermal detection system 100 that may be used for detecting elevated skin temperatures, or other thermal anomalies, that may be present within person 101 passing through a screening area. The system 100 includes a thermal imaging camera 110 that monitors a screening area through which a persons 101 to be screened pass regularly. Thermal images 151 of the individual may be captured by the thermal imaging camera 110 and displayed on a monitor 150. The display of the thermal images 151 can be calibrated such that the slightest temperature deviation above or below a normal human body temperature (98.6° F.) is displayed on a monitor 150 being watched by a health screener (not shown) in an effort to identify possible carriers of infectious diseases. As a result, the health screener may request that persons exhibiting a temperature above normal to go through additional health screening to determine the cause.

The thermal detection system 100 utilizes the nature of thermal radiation and thermal imaging in that all objects above Absolute Zero (0 Kelvin) emit at least some infrared radiation. While infrared radiation is invisible to the human eye, it can be detected and displayed by the thermal imaging camera 110. The thermal imaging camera 110 detects the infrared radiation emitted by an object and converts it into a monochromatic or multi-colored image on the monitor 150 wherein the various shades or colors represent the thermal patterns detected. If calibrated to human body temperature range, any object exhibiting radiation corresponding to temperatures beyond 98.6° F. may be displayed in shades of yellows, oranges, and reds consistent with how much higher in temperature the object is than the calibrated baseline. Likewise, any object exhibiting radiation corresponding to temperatures below 98.6° F. will be displayed in shades of blues, greens, and purples consistent with how much lower in temperature the object is than the calibrated baseline.

For example, a person 101 not having a fever (i.e., the person's skin temperature is a normal 98.6° F.) will be displayed on the monitor 150 as a neutral color (such as white) while the person's clothing or hair will appear blue, green, or purple. If the person 101 does, in fact, have a high fever, the person's exposed skin (the person's forehead, in particular) will tend toward the shades of yellow, orange, and red as the temperature of their skin is typically above the calibrated baseline. Thus, a health screener watching the monitor 150 may identify a person 101 running a fever and isolate that person 101 for further health screening.

Several problems are associated with the conventional thermal detection system 100 of FIG. 1. In particular, one problem is that the health screener must remain diligent in looking for color deviations on the monitor 150 indicating higher temperatures. Thus, if the person 101 being screened is carrying a hot cup of coffee, the coffee cup may appear yellow, orange, or red and the health screener will have to distinguish in the image between the coffee and other areas corresponding to a person's exposed skin or face. Any number of other objects may also appear in yellow, orange, or red due to the objects exhibiting temperatures above the calibrated baseline temperature (e.g., laptop computers, cell phones, hamburgers, etc.) that also must be distinguished by the health screener watching the monitor 150. As a result, the health screener must remain all the more diligent in a busy screening area.

Other problems of the conventional thermal detection system 100 include the requirement of several frames of data captured by the thermal imaging camera 110 in order to process temperature data accurately. Obtaining accurate temperature with such conventional systems 100 requires that the person 101 remain stationary for up to several seconds while data is collected. Further, the thermal imaging camera 110 may have accuracy limitations for temperature measurement. Typical accuracy specifications for temperature measurement are ±2% of target temperature or ±4° F., whichever is greater. With this in mind, a person 101 with a normal body temperature of 98.6° F. may be displayed as high as 102° F. (fever) while a person with an actual fever of may be displayed as low as 95° F. (below normal temperature).

Yet another problem is that a health screener's attention may be distracted to the point that a person having a fever is actually missed by the health screener as human error is always a factor. Other problems include a person wearing a hat not properly being screened, a person's face being turned away from the thermal imaging camera while traversing the screening area, and human mistakes being made by the health screener due to misinterpretation of the thermal images. In short, the conventional thermal detection system 100 of FIG. 1 is replete with possible failure points due to human error which results in a poor health screening system when dealing with such contagious diseases like SARS.

SUMMARY OF THE INVENTION

An embodiment of the invention is directed to a system and method for detecting a thermal anomaly in humans and/or livestock. The system includes an image capturing component that captures a visual image of incident light in a screening area, the image capturing component further operable to determine a first coordinate in the captured image, such as the location of a person's eyes. The system further includes a radiation capturing component operable to capture a thermal image of incident radiation in the screening area, the radiation capturing component further operable to determine an analysis area in the captured thermal image based upon the first coordinate in the captured light image. Finally, the system includes a processing component for determining thermal characteristics about the analysis area. As a result, if the thermal characteristics in the analysis area correspond to an alarm event, such as exceeding a threshold level of 98.6° F. which is indicative of a fever in a human, then an alarm may be triggered and the screened person or animal may be isolated for further health screening.

One goal of the method and system is to determine the location of one or both eyes during a screening process. By determining the location of the eyes, the amount of area in which the thermal characteristics is analyzed may be greatly reduced. That is, once the location of the eyes is determined in the visual data image, a specific smaller area, called the analysis area, that is above the eyes (i.e., forehead), or surrounding the eyes (i.e., nasal passages and forehead), in the corresponding thermal image data may be analyzed for thermal anomalies. Thus, instead of checking the entire thermal image for elevated temperatures, only the pertinent portion of the thermal image needs to be checked. As a result, two improvements are achieved; the amount of sheer data to be checked is greatly reduced resulting in better computing times and closer to real-time analysis; and other heated objects (i.e., coffee, laptops) will not be in the analysis area to trigger a false alarm.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The following discussion is presented to enable a person skilled in the art to make and use the invention. The general principles described herein may be applied to embodiments and applications other than those detailed above without departing from the spirit and scope of the present invention. The present invention is not intended to be limited to the embodiments shown, but is to be accorded the widest scope consistent with the principles and features disclosed or suggested herein.

Figure 2:
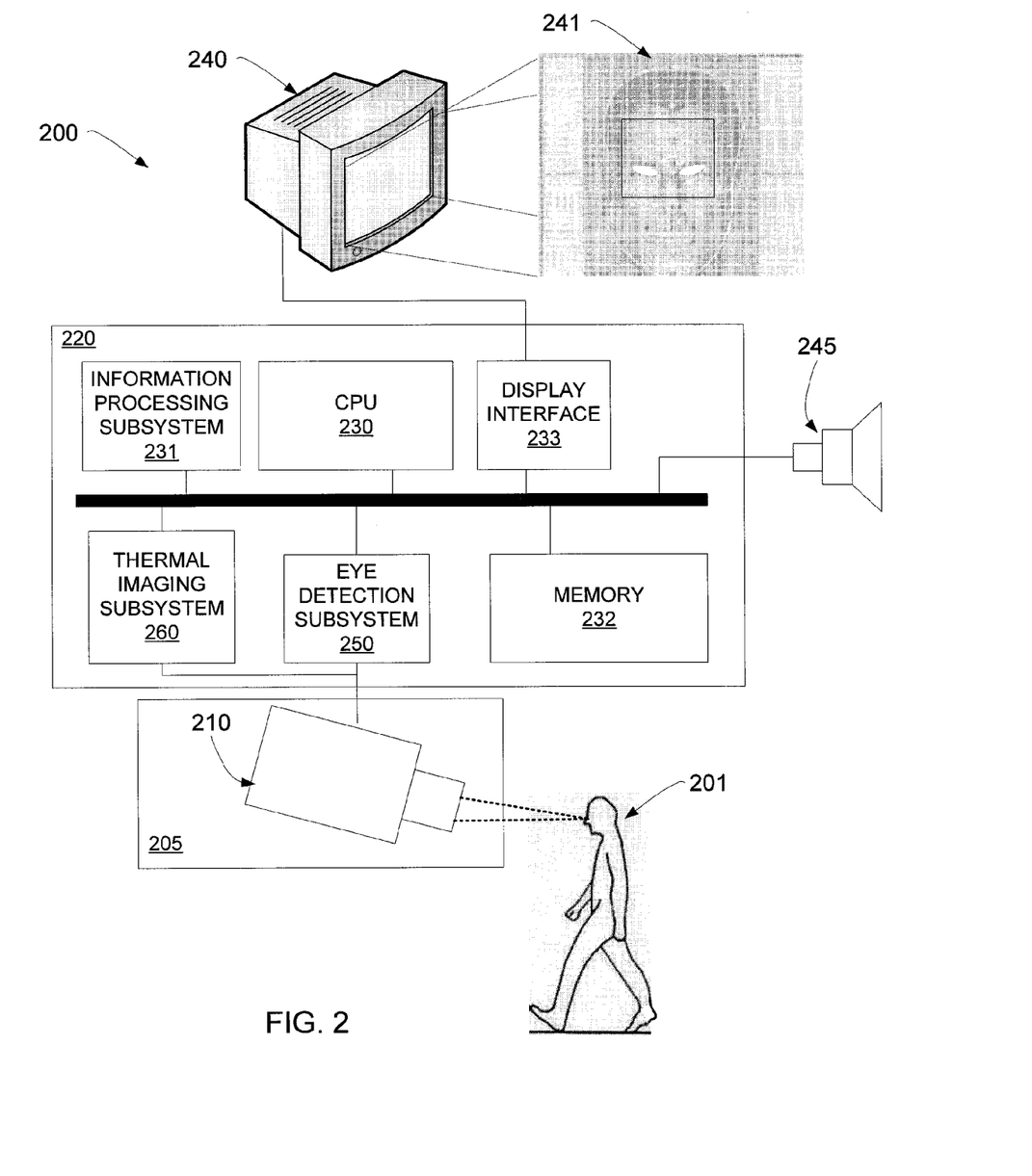
FIG. 2 is a block diagram of a thermal detection system for detecting thermal anomalies, such as elevated skin temperatures in human beings, according to an embodiment of the invention.

FIG. 2 is a block diagram of a thermal anomaly detection system 200 for detecting thermal anomalies, such as elevated skin temperatures in human beings, according to an embodiment of the invention. Typically, the system 200 may be used to screen human beings or livestock for thermal anomalies, such as an elevated temperature, i.e., a fever, and the like. Although the examples and figures in this disclosure typically refer to humans being screened, the system and method may be used with animals as well, including livestock such as cows and chickens.

The system 200 may include a camera block 200 for capturing visual and thermal data about a person 201 being screened, a processing block 220 for receiving and manipulating the data captured by the camera block 200, an alarm 245, and a monitor 240 for displaying the data and/or alarm status. Each of these components is described in greater detail below within the context of each component's respective use.

As a general overview, the system 200 of FIG. 2 is typically calibrated to provide health screening in a designated screening area of a high-traffic location such as an airport or factory-floor checkpoint. Thus, as persons 201 pass by a screening area, data about each person is collected by the camera block 205. Although not shown in FIG. 2, the system 200 may also be used to screen livestock that pass by a checkpoint area as well. The data may include both visual image data (e.g., a simple picture) and thermal image data (e.g., an infrared "heat" picture) and is passed to a processing block 220 after being captured. The processing block 220 receives the data and processes the data in specific subsystems according to the type of data. That is, visual image data is typically manipulated by an eye-detection subsystem 250 to determine specific visual characteristics of the captured image. Likewise, thermal image data is manipulated by a thermal imaging subsystem 250 to determine specific thermal characteristics of the captured image. This manipulated data is passed to an information processing subsystem 231 to determine if any thermal anomalies exist, i.e., detection of elevated skin temperatures. As such, if a thermal anomaly is detected, an alarm 245 may be activated and/or the detected thermal anomaly may be displayed on the monitor 240. This process and method is described in greater detail below with respect to FIG. 6 which follows the detailed discussion of the components of the thermal anomaly detection system 200 discussed briefly above.

As discussed in the background section above, individuals, such as the person 201, typically pass by a designated screening area that is designed to screen such persons for specific health concerns. More specifically, it is desirable to check each and every person 201 that passes by a designated screening area for elevated skin temperatures as it may be a symptom of certain infectious diseases. As such, when a person 201 enters the screening area, the camera system 205 may be focused toward the person's face and/or body to capture visual and thermal images of the person 201.

As discussed briefly above, the data to be gleaned from the person 201 by the camera block 205 includes two sets of data. The first set of data comprises a visual image of a view of the person 201 that may be used to determine certain visual characteristics, such as the location of the person's eyes within the captured view. The second set of data comprises a thermal image of the same view of the person 201 that may be used to determine certain thermal characteristics, such as the person's skin temperature within the captured view. The manipulation of the captured data is described in more detail below with respect to FIG. 3 and FIG. 4.

The camera block 205 in FIG. 2 includes a camera 210 that may be used to capture both visual and thermal data from the person 201 in the designated screening area. The visual and thermal data captured is associated with visual and thermal characteristics about objects in the screening area. Typically, the camera 210 comprises two optical paths for incident light.

A first optical path (not shown in detail) may focus incident light in the visible light range, i.e., a visual image for visual data, toward a first image capture device (not shown in detail) while a second optical path (also not shown in detail) may focus light in the infrared range, i.e., a thermal image for thermal data, toward a second image capture device (also not shown in detail).

Each image capture device may typically be a charge-coupled device (CCD) imager or a complementary metal-oxide semiconductor (CMOS) imager, although each image capture device may be any device capable of capturing the visual and thermal data used by the processing block 220. In general, CMOS imagers are less expensive than CCD imagers and CMOS devices in some cases provide better sensitivity at infrared/near-infrared wavelengths than CCD imagers. Capturing visual and thermal image data in this manner is well known in the art and will not be discussed further herein.

In another embodiment not shown, the camera block 205 may include two cameras 210 wherein each camera 210 is dedicated to its particular data capture task. That is, the camera block 205 may include a first visual imaging camera for capturing visual data and a second thermal imaging camera for capturing thermal data. As a result, in this embodiment, each camera is a stand-alone device in the camera block 205 dedicated to capturing its respective type of data.

In yet another embodiment, the camera block 205 may include a single camera 210 that has only a single optical path and a single image capture device. However, in this embodiment, additional switching circuitry enables the image capture device to employ a dual-capture mode wherein during a repeating two-step capture process, visual data is captured in the first step as the image capture device is set to capture visual data and then thermal data is captured during the second step as the image capture device is set to capture thermal data. Again, the use of image-capture devices to capture both visual and thermal data is well known in the art and will not be discussed further herein.

As visual and thermal data is collected by the camera block 205, it is passed to the processing block 220 on a data line 211. The data line 211 is typically may be a serial communications link between the camera block 205 and the processing block 220, but may also be another type of communication medium, such as a parallel communications link, an Ethernet link, a Wireless transmission link, etc. Data is received by the processing block 220 at a respective subsystem according to the type of data. That is, visual data is received by an eye-detection subsystem 250 and thermal data is received by a thermal-imaging subsystem 260. Alternatively, the data may be sent directly to a local system bus 221 (which is coupled to a processor that controls the bus 221) in the processing block 220 via a camera block interface (not shown).

The processing block 220 typically includes a central processing unit 230 (CPU) that controls the receiving, manipulating, and sending of data within the processing block 220. As is typical, the CPU 230 controls various other blocks, memories, and subsystems via a system bus 221. Thus, the CPU 230 may coordinate and controls the receiving of the visual data at the eye-detection subsystem 250 and the receiving of the thermal data at the thermal-imaging subsystem 260 either directly or through the system bus 221.

The processing block 220 may further include an information processing subsystem 231 for manipulating and analyzing the visual and thermal data received by the eye-detection subsystem 250 and the thermal-imaging subsystem 260, respectively. The information processing block 231 is also coupled to the system bus 221 and may be controlled by the CPU 230. The processing block 220 may include a memory 232 coupled to the system bus 221 and controllable by the CPU 230 for storing programs, subroutines, captured data, and manipulated data.

Once visual and thermal data is captured, manipulated and analyzed (described in detail below), the CPU 230 may coordinate the display 241 of the data on the monitor 240 via a display interface 233. Further, the CPU 230 may determine that the analysis corresponds to an alarm event and may then activate an alarm 245 coupled to the system bus 221.

Each of the above described subsystems work in conjunction with each other to provide health screening for humans or livestock by monitoring for thermal anomalies. A thermal anomaly may be an elevated skin temperature, a very low skin temperature, or any other determination that an area surrounding a detected eye or set of eyes is determined to be at a temperature outside of a normal range (e.g., ±1° from 98.6° F. for a human). A thermal anomaly, once detected may trigger an alarm 245 or some further indication (display on the monitor 240) that the screened entity should be isolated for further testing. These subsystems are described individually in more detail below.

Figure 3:
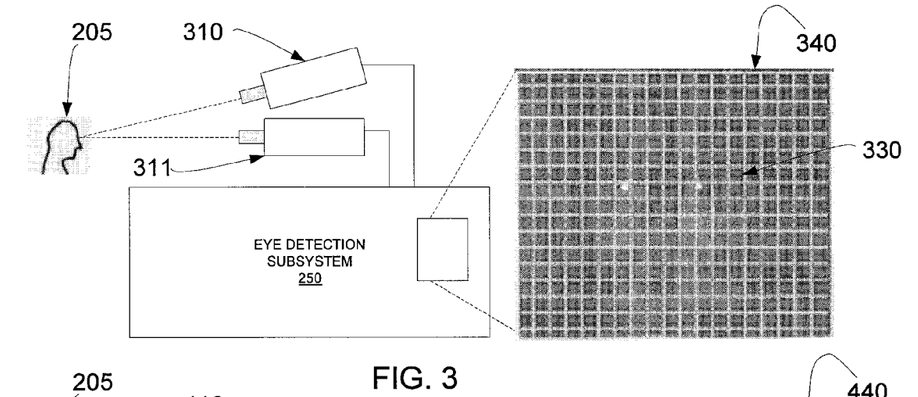
FIG. 3 is a block diagram of the eye detection subsystem of FIG. 2 according to an embodiment of the invention.

FIG. 3 is a block diagram of the eye-detection subsystem 250 of FIG. 2 according to an embodiment of the invention. Although shown in FIG. 3 as a discrete subsystem, one skilled in the art will understand that the functions of the eye-detection subsystem 250 described herein may be realized within a stand-alone computing environment, a distributed computing environment, and/or a networked computing environment. Thus, even though the eye-detection subsystem 250 of FIG. 2 is shown as entirely within the processing block 220, it is understood that this is not a limitation of the invention as the eye-detection subsystem 250 merely refers to a grouping of components designed to capture and process visual image data and may be referred to as an image capturing component or subsystem.

One goal of the eye-detection subsystem 250 is to determine the location of particular features of a human or animal, such as one or both eyes during a screening process. These features, which may also be called points of interest, once identified, assist is narrowing down the radiation detection area, or simply, he analysis area (described below). In this embodiment, by determining the location of the eyes, the amount of area in which the thermal characteristics is analyzed may be greatly reduced. That is, once the location of the eyes is determined in the visual data image, a specific smaller area, called the analysis area, that is above the eyes (i.e., forehead), or surrounding the eyes (i.e., nasal passages and forehead), in the corresponding thermal image data may be analyzed for thermal anomalies. Thus, instead of checking the entire thermal image for elevated temperatures, only the pertinent portion of the thermal image needs to be checked. As a result, two improvements are achieved; the amount of sheer data to be checked is greatly reduced resulting in better computing times and closer to real-time analysis; and other heated objects (i.e., coffee, laptops) will not be in the analysis area to trigger a false alarm.

In general, in order to determine the location of a person's eyes, two sets of visual data regarding the person's face are captured using some type of detector or imager. Then, the two sets of data can be analyzed against each other to decipher the location of the person's eyes because the human eye interacts with incident light in slightly different ways than other objects. In essence, when the person's eyes are open, the difference between two slightly different images of the person's face will highlight the pupils of the eyes because a diffuse reflection from the person's retinas is detected only in an on-axis image, (i.e., looking straight into the person's eyes produces a strong pupil signal sometimes known as "red-eye" in conventional flash photography). Thus, when a straight-on image, i.e., an "on-axis" image is compared to a slightly "off-axis" image of the person's face, other facial and environmental features are largely cancelled out, leaving the pupils 330 as the dominant feature in the differential image 340. This may be seen clearly in the differential image 340 of FIG. 3 as the person's eyes 330 as the only remaining facial features in the visual image.

Thus, in the representation shown in FIG. 3, the eye-detection subsystem 250 may include an on-axis device 310 and an off-axis device 311 that are used to produce two sets of visual data that may generate the differential image 340 needed to determine the location of a person's eyes. As will be described below in various embodiments, the on-axis device 310 and the off-axis device 311 may be stand-alone cameras, a coordinated camera system, individual imaging detectors, lights sources or any combination thereof.

A key principle in obtaining differential reflectivity from the retina of the person's eye is the dependence of retinal reflectivity on the angle between the source and the detector (this angle may be referred to as the illumination angle). Position of a light source with respect to the image sensor is subject to additional conditions. To achieve successful differencing of the images resulting in spots corresponding to the reflecting retina, it is desirable for the remainder of the field of view (including the person's face, apparel and the surroundings) to have significantly similar illumination profiles under the two different angles of illumination. For example, it is undesirable for illumination from a single-side on-axis light source to produce shadows that are significantly different than the shadows produced by a second off-axis source.

Thus, in one embodiment, the on-axis device 311 may be an imaging detector that uses incident light source that is on-axis while the off-axis device 310 may be an imaging detector that uses incident light that is off-axis. The difference in the manner in which light reflects off the person's face (and in particular the person's eyes due to the retina effect) is enough to distinguish the person's eyes from everything else in the differential image 340.

In another embodiment, the devices 310 and 311 may use light of different wavelengths. For example, the first device 310 may be an imaging detector having that uses incident light source of 800 nm while the second device 311 may be an imaging detector having that uses incident light source of 950 nm. In order to eliminate motion artifacts, the two images can be collected simultaneously if they can be distinguished by some optical property such as wavelength or polarization. The light emitted from a first light source may be at a different wavelength from the light emitted from a second light source. Thus, the light may be emitted at essentially the same time. In one such embodiment, the wavelength that yields the strongest retinal return is used by first light source (the light source associated with the on-axis device 311 whether it is, in fact, on-axis or not), and the other of the two wavelengths is used by second light source (the light source associated with the off-axis device 310). Measured on a conventional silicon-based detector, the retinal return signal is typically stronger at 800 nanometer (nm) wavelengths versus 950 nm wavelengths, and it is therefore desirable to associate the shorter wavelength with the on-axis device 311 in this case. Thus, the slight difference in the wavelength of the source of incident light is enough to distinguish the person's eyes from everything else in the differential image 340.

The differential image 340 results from the difference between the images generated using the on-axis and off-axis light sources according to one embodiment of the invention. By taking the difference between the images, relatively bright spots (i.e., the person's eyes 330) will remain against the relatively dark background when the person's eyes are open. There may be vestiges of other features of the eye remaining in the background; however, in general, the person's eyes 330 will stand out in comparison to the background. When the eyes are closed or nearly closed, there will be no bright spots in the differential image 340.

In FIG. 3, the person 205 is illustrated as directly facing the eye-detection subsystem 250. However, the person 205 may face in other directions relative to system 250. The angle formed between the direction in which person 205 is looking and the axis may be referred to as the gaze angle. The previously defined on-axis and off-axis angles do not change with gaze angle. The sensitivity of the retinal return to gaze angle is relatively weak. As such, the head and the eyes of the person 205 may frequently move relative to eye-detection subsystem 250 without significantly affecting the efficiency and reliability of the eye-detection subsystem 250.

In other embodiments, a single detector may be used with three light sources. In one such embodiment, the first light source is on-axis with the detector, and the second and third light sources are at two different off-axis angles from the detector. In this embodiment, the first and second light sources can be used in sequence to obtain one difference image, and the first and third light sources can be used to obtain a separate difference image. The use of these separate difference images facilitates discrimination between the retinal return and glare. Generally, the retinal return will be nearly the same in the separate difference images, whereas glare will not always be the same because the glare under illumination with the second light source will not necessarily be the same as glare under illumination with the third light source.

Whatever method is used to capture two sets of visual data, the eyes 330 are located by taking the difference between two images. The processing can be generally summarized as determining whether or not a bright spot exists in the differential image. Rather sophisticated processing techniques are available for analyzing images; however, these processes do not need to be used. Consequently, the processing requirements for eye-detection subsystem 250 can be reduced. In addition, because of the repetitiveness of the processing, a customized application specific integrated circuit (ASIC) or the like can be utilized by eye-detection subsystem 250. Alternatively, for CMOS detectors, the image processing may be performed on the same chip as the sensor. In any of these cases, image processing can be accomplished quickly and inexpensively.

Once the location of the eyes 330 has been determined and an analysis area is established, the thermal-imaging subsystem 260 may then capture thermal image data about the analysis area only.

Figure 4:
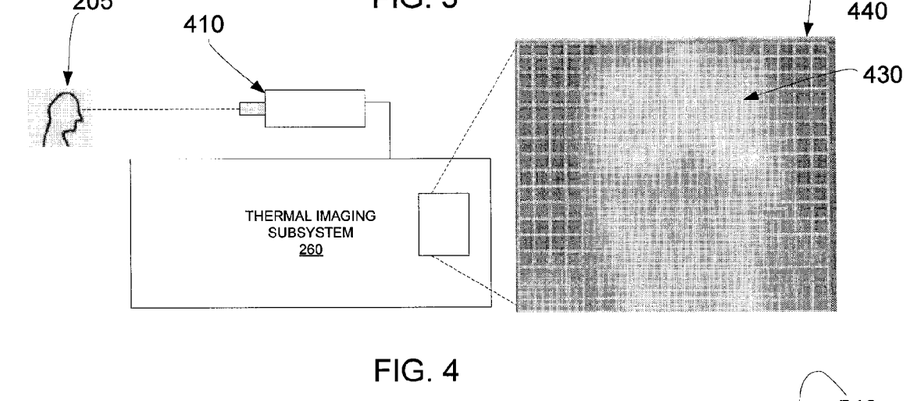
FIG. 4 is a block diagram of the thermal imaging subsystem of FIG. 2 according to an embodiment of the invention.

FIG. 4 is a block diagram of the thermal-imaging subsystem of FIG. 2 according to an embodiment of the invention. Again, although shown in FIG. 4 as a discrete subsystem, one skilled in the art will understand that the functions of the thermal-imaging subsystem 260 described herein may be realized within a stand-alone computing environment, a distributed computing environment, and/or a networked computing environment. Thus, even though the thermal-imaging subsystem 260 of FIG. 2 is shown as entirely within the processing block 220, it is understood that this is not a limitation of the invention of the invention as the thermal-imaging subsystem 260 merely refers to a grouping of components designed to capture and process thermal image data and may be referred to as a radiation capturing component or subsystem.

The thermal-imaging subsystem 260 includes a thermal imaging camera 410 that may be a part of the camera block 205 of FIG. 2. In general, the thermal-imaging camera 410 captures a thermal image, such as thermal image 440, of the person 205 that may also then be used in conjunction with the differential image 340 to analyze and detect thermal anomalies. The thermal image 440 includes a thermal representation 430 of the person's face that corresponds to the visual image captured by the eye-detection subsystem 250. Thus, in order to correlate information from the thermal image 440 to the differential image 340, the thermal-imaging camera is typically situated in close proximity to the image capture devices of the eye-detection subsystem 250. Furthermore, the thermal-imaging camera may be one-in-the-same with the visual image camera utilizing two optical paths or a switching cycle.

The data collected by the eye-detection subsystem 250, i.e., the differential image 340 having the X-Y coordinates of the detected eyes 330 identified and the data collected by the thermal imaging subsystem, i.e., the thermal image 440 is sent to the information processing subsystem (230 of FIG. 2). The information processing subsystem 231 takes the data and correlates the X-Y coordinates of the differential image to an area on the thermal image 440. As such, only the data surrounding the X-Y coordinates needs to be analyzed.

Figure 5:
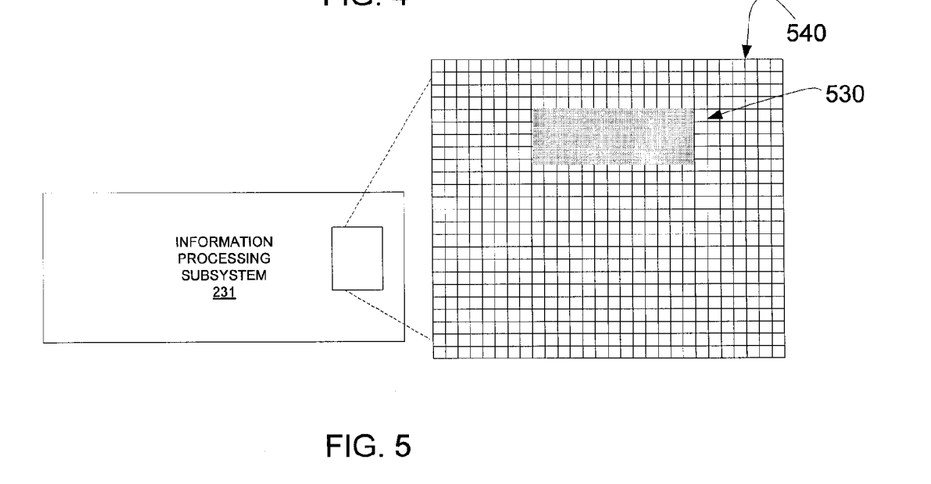
FIG. 5 is a block diagram of the information processing subsystem of FIG. 2 according to an embodiment of the invention.

FIG. 5 is an illustration of the resulting analysis image 540 used by the information processing subsystem of FIG. 2 according to an embodiment of the invention. As can be seen, only the analysis area 530 has any thermal image data shown. Thus, the information processing subsystem 231 needs only to analyze the analysis area 530 for thermal anomalies.

A number of thermal anomalies may trigger an alarm event. For example, if the temperature at any point in the analysis area 530 exceeds a threshold (e.g., 99.6° F.), an alarm may be triggered. As another example, the entire analysis area may be analyzed for temperature and if the average temperature exceeds a threshold, an alarm may be triggered. Further, the average temperature may be a moving average that is calculated based on several previous iterations of the process in order to attain more accurate results. Other thermal anomalies include detecting a high temperature without eyes, detecting very low temperatures in the analysis area 530. Still other thermal anomalies are contemplated but are not discussed herein for brevity.

Figure 6:
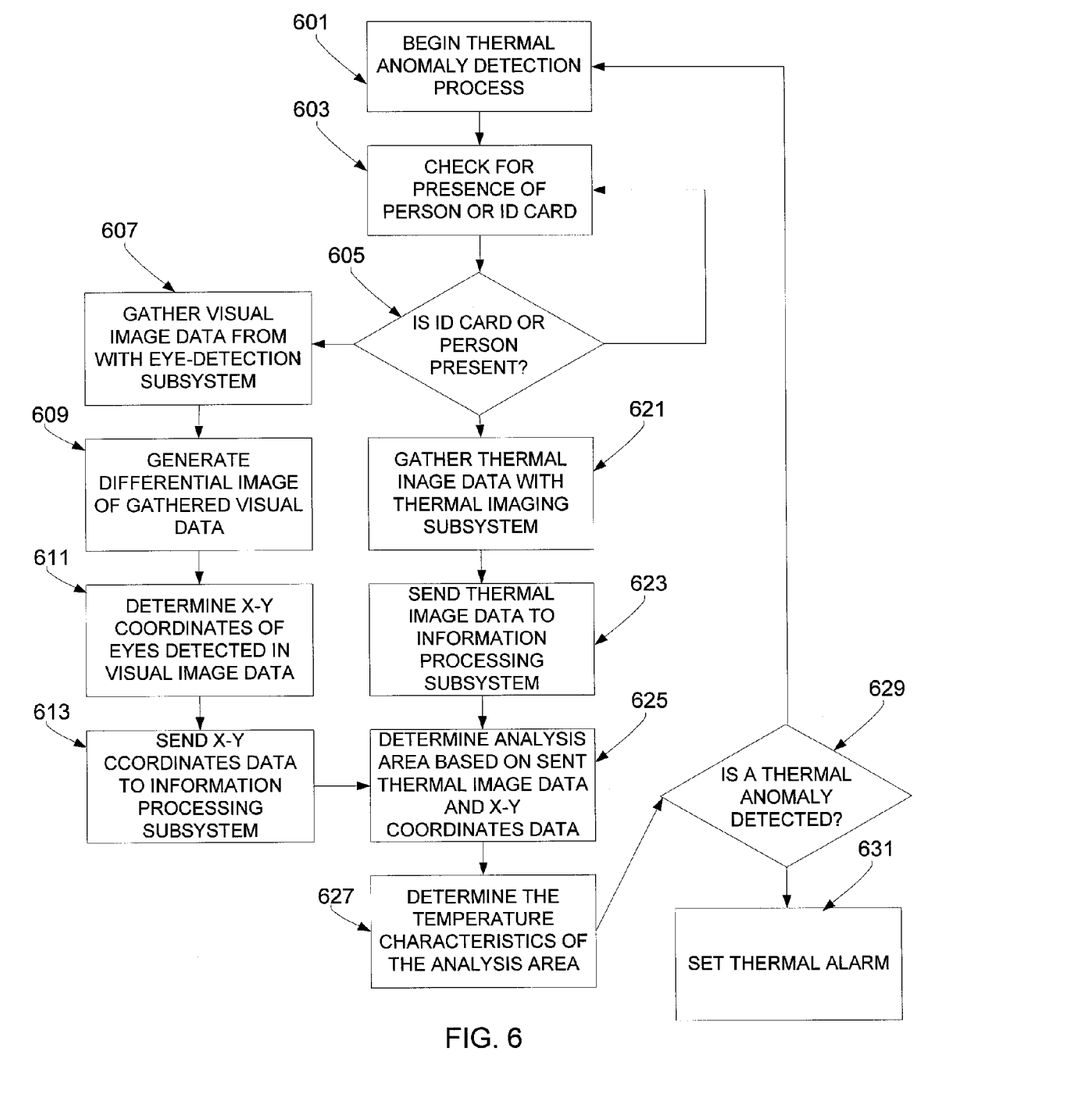
FIG. 6 is a flow chart of a method for detecting thermal anomalies in a person or livestock according to an embodiment of the invention.

FIG. 6 is a flow chart of a method for detecting thermal anomalies in a person or livestock according to an embodiment of the invention. It is understood that the method of the flow chart in FIG. 6 is one of many contemplated methods for detecting thermal anomalies and is in appreciated that the methods described herein are not limiting to the use of the system of the present invention.

The method begins at step 601 wherein a thermal anomaly detection system, such as system 200 of FIG. 2 is initiated and set to monitor a screening area for thermal anomalies. Such a screening area may be a checkpoint at an airport or factory that is arranged such that persons passing through the screening area may face a camera block for gathering both visual and thermal data about all persons passing through. As a result, at step 603, the eye-detection subsystem receives visual data gathered by the camera block and generates a differential image for the received visual data as described previously. The system may continuously check for the presence of a person by analyzing visual data gathered by the eye-detection subsystem at step 605. If a set of eyes or even a single eye is detected by the eye-detection subsystem, the method may proceed to gather additional thermal data from the screening area. If no person, i.e., no eye, is detected, then the process loops back to step 603 to gather visual data again in order achieve continuous detection. Alternatively, the system may be set up such that an ID card may be detected which activates the rest of the process. Thus, a person may insert an ID card that triggers the thermal detection process as the presence of the ID card is an indication that a person is in the screening area ready to be analyzed.

When the eye-detection subsystem detects one or more eyes, or detects the presence of an ID card, the process then simultaneously gathers thermal data from the screening area (step 621) and determines the X-Y coordinates of the location of the detected eyes (step 607). Then both the thermal data and the X-Y coordinate data are sent to the information processing subsystem in steps 623 and 613 respectively. Alternatively, all visual data may be sent to the information processing subsystem such that the information processing subsystem generates the differential image and determines the X-Y coordinates of the eyes.

At step 625, the information processing subsystem determines an analysis area based on the received (or generated) X-Y coordinates from the gathered visual data. As described previously, the analysis area may be a single point, a surrounding area or other subset of the thermal image gathered by the thermal imaging subsystem. With the analysis area determined, the information processing subsystem may then determine the temperature characteristics of the analysis area at step 627. Thus, the presence of any thermal anomalies may be determined at step 629. If no thermal anomaly is determined, then the process loops back to step 603 in order to check for the next detected eyes or ID card. If, however, a thermal anomaly is determined, such as a high average temperature in the analysis area, the process may then set a thermal alarm at step 631 and remain in an alarm state until reset by a system minder.

Figure 7:
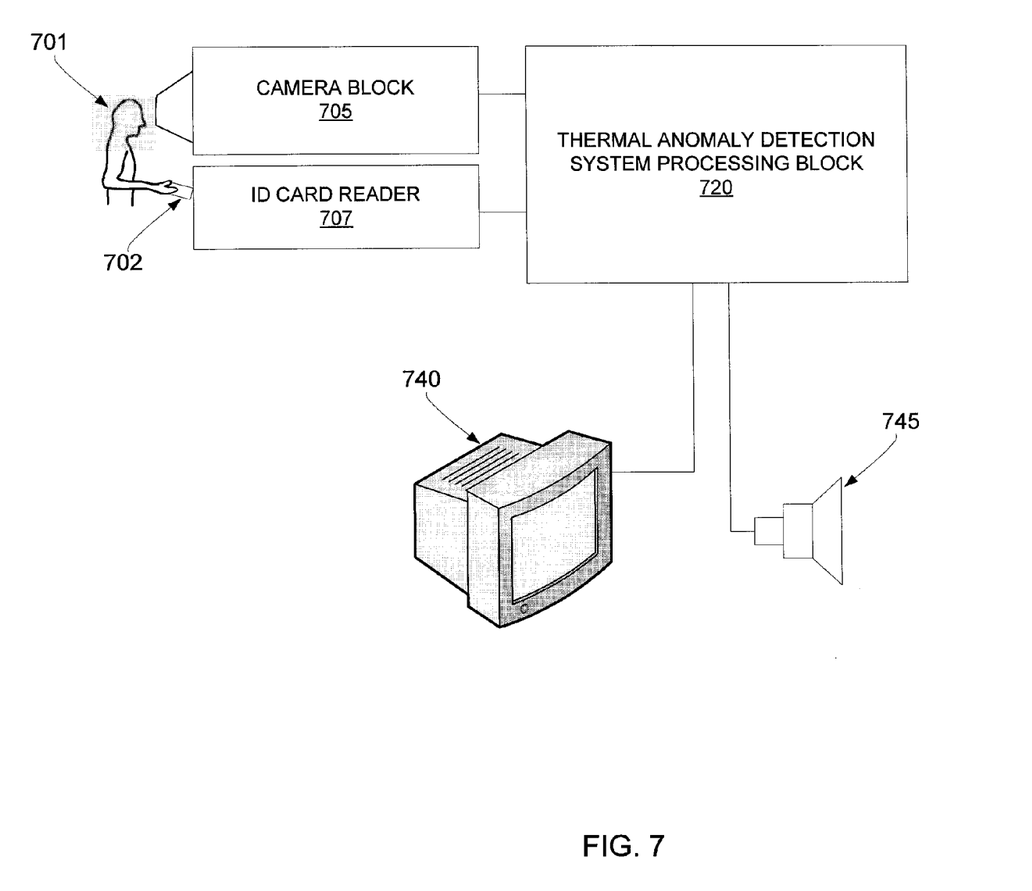
FIG. 7 is a block diagram of a thermal anomaly detection system 700 having an ID card reader as a trigger system for the anomaly detection system of FIG. 2 according to an embodiment of the invention.

FIG. 7 is a block diagram of a thermal anomaly detection system 700 having an ID card reader as a trigger system for the anomaly detection system of FIG. 2 according to an embodiment of the invention. The system includes an ID card reader 707 that is coupled to the processing block 720. As was the case above with respect to the system 200 of FIG. 2, the system 700 also includes a camera block 705 coupled to the processing block. The system may also include a monitor 740 and an alarm 745 coupled to the processing block as well.

With such a system, a person 701 having an ID card 702 may enter a screening area and insert the ID card 702 into an ID card reader 707. The insertion of the ID card may trigger the camera block 705 to gather visual and thermal data about the person as described previously. The visual and thermal data may then be sent to the processing block 720 for thermal anomaly analysis. The analysis may be displayed on the monitor and/or may trigger the alarm 745 if a thermal anomaly is detected. Thus, the person may be identified by the inserted ID card as well as requested to enter a secondary screening area to determine the cause of the thermal anomaly that was detected.

The ID card reader 707 may be any identification device capable of identifying a person or animal that is present in the screening area. In an alternative embodiment, the identification device may be a radio-frequency tag or chip attached to an animal. As such, livestock, such as cows and chickens, may be tagged with an identification device and screened in screening area prior to loading the animal onto a truck, or the like.

While the invention is susceptible to various modifications and alternative constructions, certain illustrated embodiments thereof are shown in the drawings and have been described above in detail. It should be understood, however, that there is no intention to limit the invention to the specific forms disclosed, but on the contrary, the intention is to cover all modifications, alternative constructions, and equivalents falling within the spirit and scope of the invention.

I claim:

1. A system for detecting a thermal anomaly in a desired location on an animal, comprising:
    a first imager for capturing a visual image of the animal that includes a feature;
    a second imager for capturing a thermal image of the animal; and
    a processor coupled to the first and second imagers that determines from the visual image a region encompassing the feature in the thermal image, that identifies based on the determined region, a second region, in the thermal image, and that analyzes the second region for the thermal anomaly,
wherein the second region does not include the feature.

2. The system of claim 1, wherein the animal is one of a human or a live stock.

3. The system of claim 1, wherein the processor analyzes an area surrounding an eye of the animal, as the second region.

4. The system of claim 1, wherein the processor generates a signal if thermal characteristics of the second region exceed a predetermined threshold.

5. The system of claim 4, wherein the predetermined threshold corresponds to an upper limit of a nominal range of temperature of the animal.

6. The system of claim 1, wherein the first and second imagers simultaneously capture visual and thermal images, respectively.

7. A method for detecting a thermal anomaly on an animal, the method comprising:
passing the animal through a screening area;
capturing, by one or more imagers, a visual image and a thermal image of the animal, as the animal passes through the screening area;
identifying a region of interest in the visual image;
determining, based on the region of interest in the visual image, a corresponding region of interest in the thermal image;
identifying, based on the determined region of interest, a second region of interest in the thermal image;
analyzing the second region of interest for the thermal anomaly; and
outputting the analysis,
wherein the analyzing of the second region of interest does not include analysis of the determined region of interest.

8. The method of claim 7, wherein the capturing of the visual image includes capturing a plurality of the visual images to generate a differential visual image, as the visual image.

9. The method of claim 7, wherein:
the capturing of the visual image includes:
capturing a first visual image from a first perspective with respect to the animal, and
capturing a second visual image from a different perspective than the first perspective; and
the identifying of the region of interest in the visual image includes:
generating the visual image as a differential image of the first and second visual images, and
detecting a dominant feature in the visual image as the region of interest.

10. The method of claim 7, further comprising:
automatically blocking entry of the animal responsive to the analyzed second region of interest showing the thermal anomaly.

11. The method of claim 10, wherein the analyzing of the second region of interest is completed in real-time to allow opening of an access point for entry of the animal.

12. The method of claim 7, wherein the outputting includes indicating when the second region of interest associated with the animal has a temperature exceeding a first threshold temperature.

13. The method of claim 12, further comprising actuating an alarm responsive to the temperature of the second region of interest exceeding the first threshold temperature or a second threshold temperature above the first threshold temperature.

14. A thermal anomaly detection system for detecting whether a temperature of an animal exceeds a threshold level, comprising:
a combination visual and thermal imager configured to capture a visual image of the animal that includes a feature and a thermal image of the animal; and
a processor coupled to the imager that determines from the visual image a region encompassing the feature in the thermal image and configured to identify, based on the feature in the visual image, a second region in the thermal image and to analyze the second region which is less than the entire thermal image for a thermal anomaly,
wherein the analyzed second region does not include the feature associated with the visual image.

15. The system of claim 14, further comprising a monitor for displaying the visible and thermal images.

16. The system of claim 14, further comprising an access point configured to open responsive to the analyzed region of the thermal image not showing any thermal anomaly and to be closed responsive to the analyzed region of the thermal image showing the thermal anomaly.

17. The system of claim 14, wherein the combination imager includes at least one CMOS image array.

18. The system of claim 14, further comprising an identification unit configured to identify the animal prior to initiating the capturing of the images by the imager.

19. The system of claim 18, wherein the identification unit identifies an identification card or a radio frequency identification tag.

* * * * *